US00PP14497P29

(12) United States Plant Patent
Pierce

(10) Patent No.: US PP14,497 P2
(45) Date of Patent: Jan. 27, 2004

(54) CALIBRACHOA PLANT NAMED 'CAL WHITE'

(50) Latin Name: *Calibrachoa spp.*
Varietal Denomination: Cal White

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,219

(22) Filed: Mar. 13, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Jondle & Associates, PC

(57) ABSTRACT

'Cal White' is a new variety of Calibrachoa plant. This new variety has white colored flowers.

1 Drawing Sheet

Genus and species: *Calibrachoa spp.*
Variety denomination: 'Cal White'.

BACKGROUND OF THE INVENTION

'Cal White' originated from a hybridization made in the year 2000 in Gilroy, Calif. The female parent was a Calibrachoa breeding line with rose colored flowers known as 3-2 a proprietary line unnamed and unpatented. The male parent was Calibrachoa variety 77-3 an ivory white proprietary line unnamed and unpatented.

'Cal White' is a product of a planned breeding program intended to create new calibrachoa plants with white colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF THE GENUS CALIBRACHOA LLAVE & LEX

The genus Petunia was originally established in 1803 by A. L. Jussieu, who described both *P. parviflora* and *P. nyctaginifloa* as type species. Using a non-horticultural system that selected the first mentioned species as the type species (*lectotype*), N. L. Britton and H. A. Brown declared *P. parviflora* as the type species for Petunia in 1913.

During the 1980's and 1990, H. J. Wijsman published a series of articles regarding the ancestry of *P. hybrida,* the Garden Petunia, and the inter-relationship of several species classified as Petunia. These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the *lectotype* species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the *lectotype* species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

DETAILED DESCRIPTION OF THE NEW PLANT

The following traits and characteristics describe the new variety. The plant history was taken on 7 month old plants that were cut back numerous times prior to data readings being taken.

Classification:
*Family.*—Solanaceae.
*Species.*—*Calibrachoa spp.*
Growth:
*Form.*—Semi upright and decumbent.
*Habit.*—Good vigorous habit, well branched, full plant.
*Height.*—5–10 cm.
*Width.*—45–55 cm.
*Time to produce a finished flowering plant.*—9–11 weeks.

*Outdoors plant performance.*—Full sun, free flowering though the summer, some heat tolerance, used as a hanging plant; in mixed container plantings; mass planting in a bed.

*Time to initiate and develop roots.*—18–23 days.

Stems:

*Stem color.*—R.H.S. 144A (yellow-green).

*Stem length.*—35–50 cm.

*Stem diameter.*—0.2–0.3 cm.

*Stem internodes length.*—0.5–4.0 cm.

*Stem texture.*—Glandular hairs of various sizes.

*Stem anthocyanin.*—No.

*Pedicel color.*—RHS 144A (yellow-green).

*Pedicel length.*—2.1–2.9 cm.

*Pedicel diameter.*—0.1 cm.

*Pedicel texture.*—Glandular hairs of various sizes.

Leaves:

*Arrangement.*—Alternate; upper leaves sub-opposite.

*Leaf color.*—Upper side, RHS 137A (green). Underside, RHS 191A (greyed-green) but a little more green.

*Leaf length.*—3.0–4.0 cm.

*Leaf width.*—1.0–1.6 cm.

*Leaf blade shape.*—Oblong/Elliptic.

*Leaf margin.*—Entire.

*Leaf apex aspect.*—Obtuse.

*Leaf base aspect.*—Acuminate.

*Leaf texture.*—Sparse glandular hairs.

*Venation.*—Pinnate.

*Venation color.*—RHS 144A (yellow-green).

*Petiole color.*—RHS 144A (yellow-green).

*Petiole length.*—0.2–0.3 cm.

*Petiole width.*—0.1–0.15 cm.

*Petiole texture.*—Sparse glandular hairs.

Bud:

*Color at tight bud.*—RHS 154C (yellow-green).

*Bud shape.*—Oblong.

*Bud diameter.*—0.3–0.5 cm.

*Bud length.*—1.0–1.7 cm.

Flowers:

*Blooming habit.*—Continuous throughout the growing season. Good floriferousness.

*Inflorescence type.*—Flowers solitary in upper leaf axis.

*Floret type.*—Funnel form, 5 lobed petals, fused at base.

*Young flower color.*—Pure white, subdued RHS N144A (yellow-green) Mid-veins.

*Young flower floret diameter.*—2.2–2.5 cm.

*Mature flower color.*—Front side, Pure white; RHS N144A (yellow-green) mid-veins.

*Mature flower color.*—Underside, Pure white; RHS N144B (yellow-green) mid-veins.

*Corolla tube color inside.*—RHS 7A (yellow); subdued RHS N144A (Yellow-green) mid-veins; RHS 151D (yellow-green) secondary veins, but lighter.

*Corolla tube length.*—1.6–1.8 cm.

*Corolla outside texture.*—Glandular hairs various sizes.

*Flower (limb) diameter.*—2.5–2.8 cm.

*Petal apex shape.*—Slightly retuse.

*Petal base shape.*—Fused.

*Petal margin.*—Entire.

*Waviness of petals.*—None.

*Petal lobation.*—Moderate.

*Petal texture.*—Papillose.

*Sepals.*—5.

*Sepal color.*—RHS 143A (green).

*Sepal length.*—1.0–1.1 cm.

*Sepal width.*—2.5–0.3 cm.

*Sepal shape.*—Oblong.

*Sepal apex.*—Acute.

*Sepal texture.*—Glandular hairs various sizes.

*Lastingness of individual blooms.*—5–8 days.

*Fragrance.*—None.

Reproductive organs:

*Stamens.*—5; 2 taller, 3 shorter.

*Filament color.*—RHS 145D (yellow-green).

*Pollen color.*—RHS 13B (yellow).

*Pistil.*—One.

*Stigma color.*—RHS 143C (green).

*Style color.*—RHS 145C (yellow-green).

*Fruit seed set.*—Not observed.

COMPARISON WITH MOST SIMILAR VARIETY

'Cal White' differs from the female parent 3-2 in the following ways: 'Cal White' has white flowers and 3-2 has rose flowers. 'Cal White' has smaller leaves and has a more prostrate habit than 3-2.

'Cal White' differs from the male parent 77-3 in the following ways: 'Cal White' has bright white flowers and 77-3 has ivory white flowers. 'Cal White' flowers earlier and has larger leaves than 77-3.

What is claimed is:

1. A new and distinct Calibrachoa plant as shown and described herein.

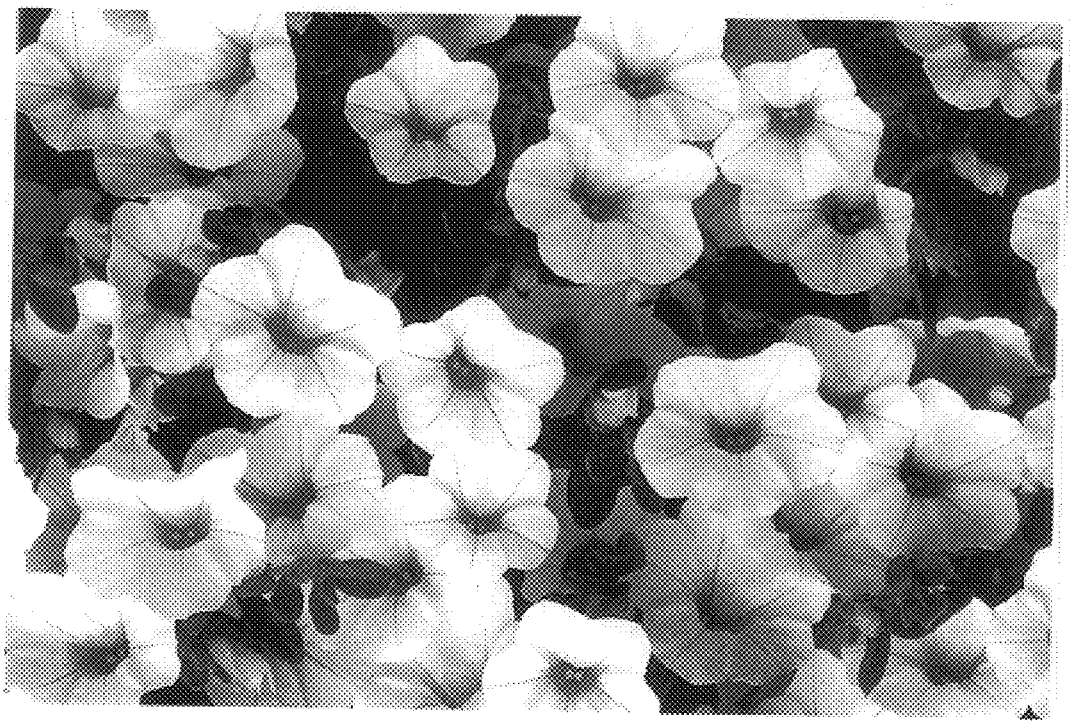

* * * * *